(12) United States Patent
Garcia et al.

(10) Patent No.: US 9,072,563 B2
(45) Date of Patent: Jul. 7, 2015

(54) FASTENER INSERTION METHOD

(71) Applicant: BIOMET MICROFIXATION, LLC, Jacksonville, FL (US)

(72) Inventors: Saddy R. Garcia, St. Augustine, FL (US); Ryan N. Luby, Jacksonville, FL (US)

(73) Assignee: Biomet Microfixation, LLC, Jacksonville, FL (US)

( * ) Notice: Subject to any disclaimer, the term of this patent is extended or adjusted under 35 U.S.C. 154(b) by 0 days.

(21) Appl. No.: 13/916,030

(22) Filed: Jun. 12, 2013

(65) Prior Publication Data
US 2013/0274816 A1   Oct. 17, 2013

Related U.S. Application Data

(63) Continuation of application No. 12/040,310, filed on Feb. 29, 2008, now abandoned.

(60) Provisional application No. 60/905,157, filed on Mar. 6, 2007, provisional application No. 60/904,678, filed on Mar. 2, 2007.

(51) Int. Cl.
*A61B 17/88* (2006.01)
*A61B 17/86* (2006.01)
*B25B 23/14* (2006.01)
*A61B 19/00* (2006.01)

(52) U.S. Cl.
CPC ............ *A61B 17/8886* (2013.01); *A61B 17/86* (2013.01); *A61B 17/866* (2013.01); *A61B 17/8875* (2013.01); *A61B 2019/307* (2013.01); *B25B 23/1415* (2013.01); *A61B 17/861* (2013.01)

(58) Field of Classification Search
CPC ... A61B 17/86; A61B 17/861; A61B 17/8886
USPC .................................... 606/80, 104, 300–331
See application file for complete search history.

(56) References Cited

U.S. PATENT DOCUMENTS

| | | | |
|---|---|---|---|
| 5,101,698 A | 4/1992 | Paradiso | |
| 5,224,230 A | 7/1993 | Vanicsek et al. | |
| 5,350,026 A | 9/1994 | Markus et al. | |
| 5,409,376 A | 4/1995 | Murphy | |
| 5,725,533 A * | 3/1998 | Carlsson | 606/101 |
| 5,928,236 A | 7/1999 | Augagneur et al. | |
| 5,971,987 A * | 10/1999 | Huxel et al. | 606/916 |
| 6,132,435 A | 10/2000 | Young | |
| 6,547,500 B2 | 4/2003 | Cosenza et al. | |

(Continued)

FOREIGN PATENT DOCUMENTS

| | | |
|---|---|---|
| EP | 1557576 A1 | 7/2005 |
| WO | 97-28927 A1 | 8/1997 |

OTHER PUBLICATIONS

Office Action regarding U.S. Appl. No. 12/040,310 mailed Jan. 6, 2012.
Non-Final Office Action regarding U.S. Appl. No. 12/040,310, mailed Jun. 15, 2012.
Final Office Action regarding U.S. Appl. No. 12/040,310, mailed Dec. 14, 2012.

(Continued)

*Primary Examiner* — Christopher Beccia
(74) *Attorney, Agent, or Firm* — Harness, Dickey

(57) ABSTRACT

A method is provided and may include rotating a biocompatible, non-metallic threaded fastener at a rotational speed greater than 15,000 revolutions per minute and driving said fastener into a bone at said rotational speed.

20 Claims, 2 Drawing Sheets

(56) References Cited

U.S. PATENT DOCUMENTS

| | | |
|---|---|---|
| 7,708,505 B2 | 5/2010 | Opsitos, Jr. et al. |
| 2004/0018471 A1 | 1/2004 | Giorno |
| 2005/0019730 A1* | 1/2005 | Gittleman .................... 433/174 |
| 2005/0149031 A1 | 7/2005 | Ciccone et al. |
| 2006/0039772 A1 | 2/2006 | Matthys-Mark |
| 2007/0100336 A1* | 5/2007 | McFarlin et al. ............... 606/45 |

OTHER PUBLICATIONS

International Search Report dated Jun. 9, 2008 regarding International Application No. PCT/US2008/02746.

Written Opinion of the International Searching Authority dated Jun. 9, 2008 regarding International Application No. PCT/US2008/02746.

* cited by examiner

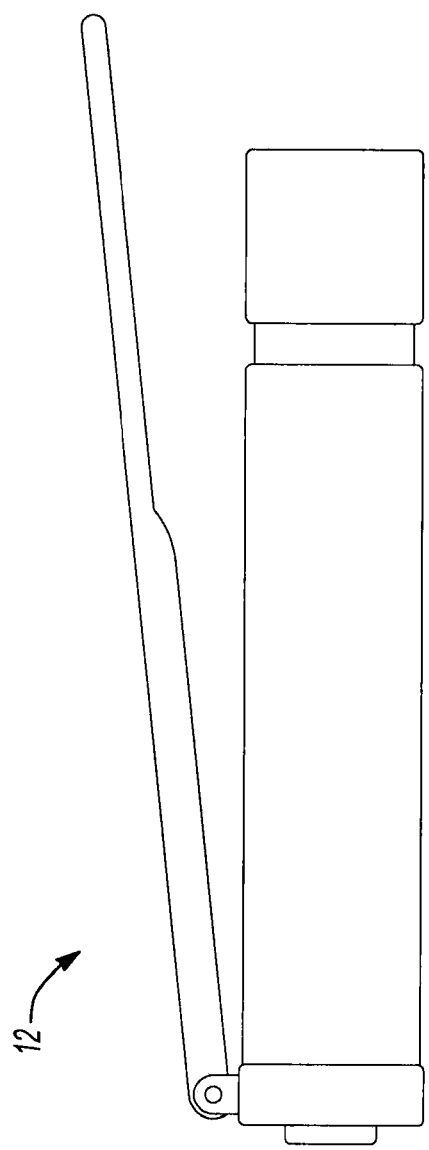

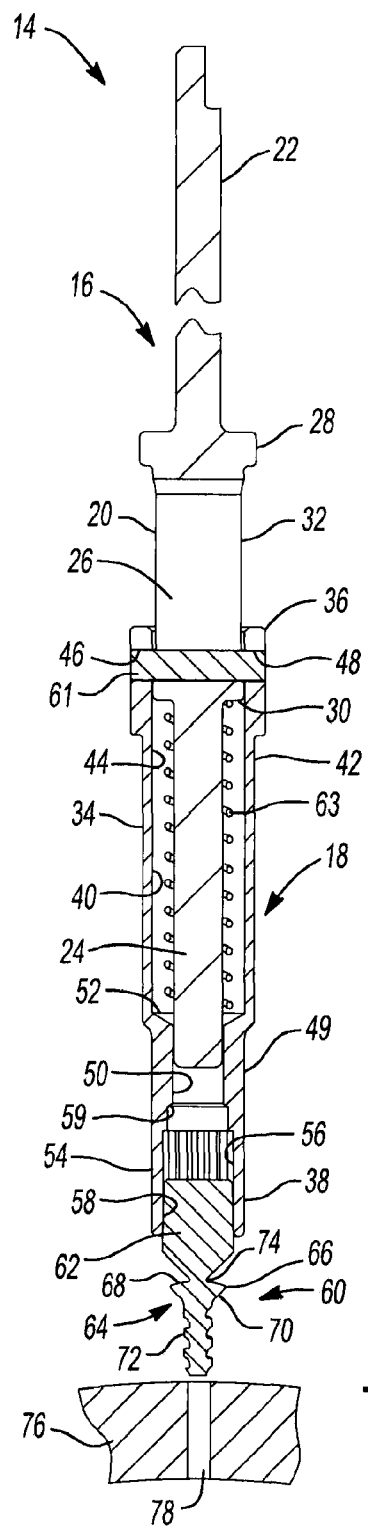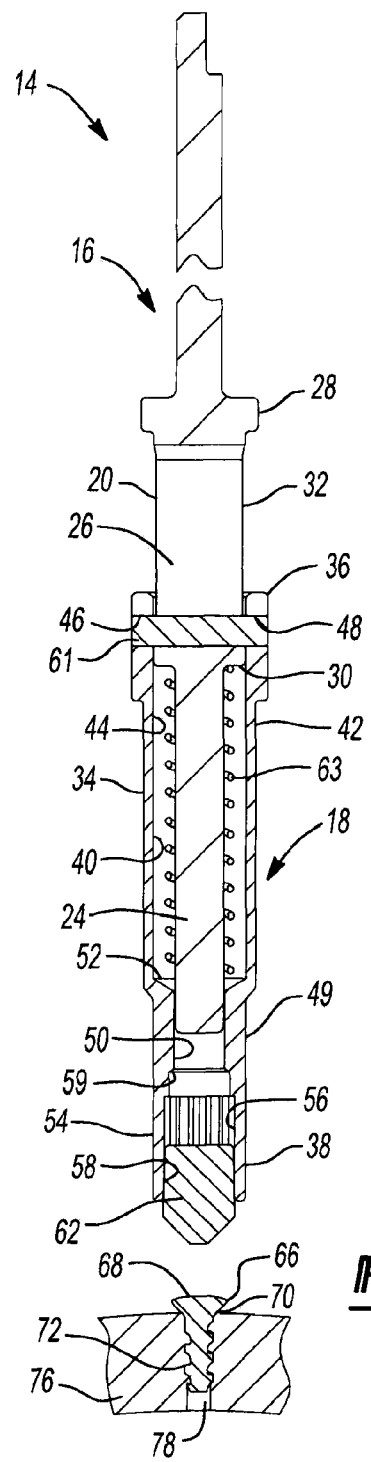

FASTENER INSERTION METHOD

CROSS-REFERENCE TO RELATED APPLICATIONS

This application is a continuation of U.S. patent application Ser. No. 12/040,310, filed on Feb. 29, 2008, which claims the benefit of U.S. Provisional Application No. 60/905,157, filed on Mar. 6, 2007, and U.S. Provisional Application No. 60/904,678, filed on Mar. 2, 2007. The disclosures of each of the above applications are incorporated herein by reference.

FIELD

The present disclosure relates to threaded fasteners, and more specifically to insertion methods for threaded fasteners.

BACKGROUND

The statements in this section merely provide background information related to the present disclosure and may not constitute prior art.

Typical fastener insertion techniques may include applying a torque to a threaded fastener to rotationally drive the fastener into a structure. The torsional strength of the fastener is typically greater than the torque applied to drive the fastener to prevent breaking of the fastener before insertion is completed. The torque applied to the fastener increases when a self-tapping fastener is used due to the additional force required to cut threads into the structure.

SUMMARY

A method is provided and may include rotating a biocompatible, non-metallic threaded fastener at a rotational speed greater than 15,000 revolutions per minute and driving said fastener into a bone at said rotational speed.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a perspective view of a powered driver according to the present disclosure;

FIG. 2 is a translucent plan view of an adapter assembly and fastener according to the present disclosure; and FIG. 3 is an additional translucent plan view of the adapter assembly and fastener of FIG. 2.

DETAILED DESCRIPTION

The following description is merely exemplary in nature and is not intended to limit the present disclosure, application, or uses.

With reference to FIGS. 1-3, a driving assembly for a fastener may include a powered driver 12 and an adapter assembly 14. Powered driver 12 may be any driver capable of driving adapter assembly 14 in the manner discussed below. Powered driver 12 shown in FIG. 1 is a powered driver from MicroAire Surgical Instruments L.L.C. of Charlottesville, Va. Adapter assembly 14 may be engaged with and driven by powered driver 12.

More specifically, adapter assembly 14 may include a plunger 16 and a driving member 18. Plunger 16 may include a central body portion 20, a connection shank 22, and an ejector shaft 24. Central body portion 20 may include a generally cylindrical body 26 having first and second ends 28, 30. An elongate passage 32 may extend radially through cylindrical body 26 and may have an axial extent along cylindrical body 26. Connection shank 22 may extend axially from first end 28 of cylindrical body 26 and may engage powered driver 12 for driving adapter assembly 14. Ejector shaft 24 may be generally cylindrical or may be in the form of a drill bit for drilling a pilot hole, as discussed below, and may extend axially from second end 30 of cylindrical body 26 and may be slidably disposed within driving member 18, as discussed below.

Driving member 18 may include an elongate body 34 having first and second ends 36, 38. A central opening 40 may extend axially through elongate body 34 and first and second ends 36, 38. A first portion 42 of elongate body 34 may include a first portion 44 of central opening 40 passing therethrough. First portion 44 of central opening 40 may extend through first end 36 and may have a first diameter greater than the diameter of a central portion of cylindrical body 26 and second end 30 thereof and less than the diameter of first end 28 of cylindrical body 26. A set of apertures 46, 48 may extend radially through first portion 42 of driving member 18 near first end 36.

A second portion 49 of elongate body 34 may include a second portion 50 of central opening 40 passing therethrough. Second portion 50 of central opening 40 may have a second diameter that is less than the first diameter of first portion 44, forming a step 52 therebetween. The second diameter of second portion 50 may be greater than the diameter of ejector shaft 24 and less than the diameter of cylindrical body 26 of plunger 16.

A third portion 54 of elongate body 34 may include a driving geometry. More specifically, third portion 54 may include a third portion 56 of central opening 40 extending therethrough. Third portion 56 may extend through second end 38 of driving member 18 and may define a series of flats 58 or some other form of driving geometry on an inner wall of third portion 56. Third portion 56 of central opening 40 may have a third diameter that is greater than the second diameter of second portion 50, forming a step 59 therebetween.

Cylindrical body 26 may be disposed in first portion 44 of central opening 40 and a pin 61 may pass through apertures 46, 48 in driving member 18 and elongate passage 32 in plunger 16, slidably coupling plunger 16 to driving member 18. Ejector shaft 24 may extend into first and second portions 44, 50 of central opening 40 when plunger 16 is in a retracted position (seen in FIGS. 2 and 3) and may be extended into third portion 56 of central opening 40 to abut and/or eject a fastener 60, as discussed below. A spring 63 may be engaged with step 52 and second end 30 of cylindrical body 26, urging plunger 16 into the retracted position.

Fastener 60 may be disposed within third portion 56 of central opening 40. Fastener 60 may include a torque limiting feature, such as first and second portions that are removable from one another when a predetermined torque limit is exceeded. For example, the first portion may include a breakaway portion 62 and the second portion may include a fastening portion 64. Breakaway portion 62 may be coupled to fastening portion 64 and may include a series of flats engaged with flats 58 within third portion 56 of central opening 40, providing for driving of fastener 60 by the driving assembly. Breakaway portion 62 may be retained within third portion 56 of central opening 40 through an interference fit engagement therewith. Fastening portion 64 may include a head 66 having upper and lower portions 68, 70 and a threaded shank 72. Breakaway portion 62 may be integrally formed with and coupled to upper portion 68 of head 66 at a reduced diameter breakaway region 74 and threaded shank 72 may extend from lower portion 70. A series of recesses (not shown) may be formed in a perimeter of head 66.

Fastener 60 may be formed from a variety of materials including, but not limited to metals (including titanium, titanium alloys, stainless steel, zirconium, and CoCr), biocompatible non-resorbable materials (including polyetheretherketone (PEEK) and polyetherketoneketone (PEKK)), biocompatible resorbable materials, ceramics, composite materials, allograft or xenograft (including demineralized bone matrix and coral), or combinations thereof.

The fasteners and fastener insertion method discussed below may include a variety of applications such as to craniofacial procedures, neurosurgical procedures, spinal procedures, orthopedic procedures, suture anchors (Glencord anchors), small bone fixation/anchors, anterior cruciate ligament (ACL) fixation devices (tendon repair devices), and soft tissue anchors. Further, while discussed with respect to powered driver 12, adapter assembly 14, and fastener 60, it is understood that a variety of alternate driving assemblies and fasteners may be used as well.

As seen in FIGS. 2 and 3, fastener 60 may be fixed to another structure 76 such as bone, wood, or some other media. A pilot hole 78 may be drilled into structure 76 and fastener 60 may be inserted into pilot hole 78. More specifically, fastener 60 may cut threads into pilot hole 78. Fastener 60 may therefore act as a self tapping screw. In order to insert a self-tapping screw, work is performed on the screw. Work is generally defined as a force imparted over a distance:

$$Work = F_i \times D;$$

where $F_i$ is force and D is distance.

In the context of the present disclosure, the force ($F_i$) noted above in the work definition may generally include a sum of the force ($F_c$) needed to cut (or tap) threads and the force of friction ($F_{f1}$) from the threads on structure 76. The driving assembly may apply the force ($F_i$) to fastener 60 in order to insert fastener 60 into pilot hole 78. The force ($F_s$) applied by fastener 60 may generally include the sum of the force ($F_t$) from the torque imparted on fastener 60 and the force ($F_k$) from the kinetic energy of fastener 60. Therefore, in order to insert fastener 60 into structure 76, force ($F_e$) should be greater than force ($F_i$). When fastener 60 is inserted at low rotational speeds, the kinetic energy force component ($F_k$) may be small relative to the torque force component ($F_t$).

Kinetic energy is generally defined as:

$$K = \tfrac{1}{2} I \omega^2;$$

where K is kinetic energy, I is moment of inertia, and w is angular rotational velocity. Angular rotational velocity is directly proportional to rotational speed. Therefore, the kinetic energy force component ($F_k$) may be directly proportional to the square of the rotational speed that fastener 60 is being driven at. As rotational speed of fastener 60 increases, the torque force component ($F_t$) needed to drive fastener 60 into structure 76 may be reduced. More specifically, fastener 60 may be driven at a rotational speed that reduces the torque force component ($F_t$) required to drive fastener 60 into structure 76 below the torsional strength of fastener 60. As such, fastener 60 may cut threads into structure 76, even where structure 76 has a torsional resistance that is greater than the torsional strength of fastener 60.

However, once fastener 60 is fully inserted into structure 76 and head 66 abuts structure 76, the force ($F_i$) required to further insert fastener 60 into structure 76 may be increased by the force of friction ($F_{f2}$) from head 66 on structure 76. In order to maintain rotation of fastener 60, force ($F_s$) must be increased. If the rotational speed that fastener 60 is being driven at remains constant, the torque force component ($F_t$) increases. Once the torque force component ($F_t$) exceeds the torsional strength of breakaway region 74, breakaway portion 62 may be separated from fastening portion 64. Alternatively, some other torque limiting feature of fastener 60 or the driving assembly may prevent further transmission of driving torque to fastening portion 64.

However, the force ($F_s$) applied to drive fastener 60 may be limited such that it is greater than the sum of the force ($F_c$) needed to cut (or tap) threads and the force of friction ($F_{f1}$) from the threads on structure 76, but less than a strip-out force ($F_{so}$), ($F_{so} > F_s > F_c + F_{f1}$). Strip-out may occur when fastener 60 is located within structure 76 and rotationally driven without further insertion into structure 76. In order to avoid a strip-out condition once fastener 60 is inserted into structure 76 and fastener head 66 is seated against structure 76, the force applied to fastener 60 ($F_s$) may be limited such that it is less than the sum of the force ($F_c$) needed to cut (or tap) threads, the force of friction ($F_{f1}$) from the threads on structure 76, and the force of friction ($F_{f2}$) from head 66 on structure 76, which is less than the strip-out force ($F_{so}$), ($F_{so} > F_c + F_{f1} + F_{f2} > F_s$).

While discussed with regard to pilot hole 78, the arrangement discussed above may also be used where fastener 60 is a self-drilling fastener and there is no pilot hole. In the self-drilling configuration, the discussion above applies equally, except the force ($F_i$) needed to drive fastener 60 may be increased by a drilling force ($F_d$). Accordingly, the kinetic energy force component ($F_k$) of fastener 60 may also be increased in order to keep the torque force component ($F_t$) below the torsional strength of fastener 60.

Pilot hole 78 may have a diameter that is greater than the minor diameter and less than the major diameter of fastener 60. The rotational speed needed to drive fastener 60 may vary based on the relation between the size of pilot hole 78, the major diameter of fastener 60, the length of threaded shank 72, and the material density of structure 76 relative to the material density of fastener 60.

More specifically, as the diameter of pilot hole 78 is increased, the rotational speed needed to drive fastener 60 is reduced and as the diameter of pilot hole 78 is decreased, the rotational speed needed to drive fastener 60 is increased. Similarly, as the length of threaded shank 72 is increased, the rotational speed needed to drive fastener 60 is increased and as the length of threaded shank 72 is decreased, the rotational speed needed to drive fastener 60 is decreased. As the material density of structure 76 is increased relative to the material density of fastener 60, the rotational speed needed to drive fastener 60 is increased and as the material density of structure 76 is decreased relative to the material density of fastener 60, the rotational speed needed to drive fastener 60 is decreased.

In operation, adapter assembly 14 may be coupled to powered driver 12 and a desired driving speed may be selected for powered driver 12. Fastener 60 may be loaded into adapter assembly 14 and an end of fastener 60 may be placed against an opening of pilot hole 78 and fastener 60 may be axially aligned with pilot hole 78. Fastener 60 may then be driven into pilot hole 78, as discussed above.

More specifically, powered driver 12 may be rapidly actuated, rather than gradually actuated, to quickly generate a desired rotational speed. Downward force may be applied to fastener 60 by displacement of plunger 16 into engagement with fastener 60 once powered driver 12 has been actuated to achieve the desired rotational speed to drive fastener 60 into structure 76. Fastener 60 may be formed from a material that has a greater or lesser torsional strength than the torsional resistance of structure 76. However, even when fastener 60 is formed from a material having a lesser torsional strength than the torsional resistance of structure 76, fastener 60 may still be driven into pilot hole 78 and may tap pilot hole 78 due to the kinetic energy force component ($F_k$) and the torque force component ($F_t$) of fastener 60, as discussed above.

More specifically, when fastener 60 is driven into pilot hole 78 at a high rotational speed, the force ($F_s$) applied by fastener 60 may be great enough to tap structure 76, such as bone. As indicated above, when the rotational speed of fastener 60 is great enough, the kinetic energy force component ($F_k$) may reduce the torque force component ($F_t$) needed to drive fastener 60 to a level below the torsional strength of fastener 60. Since the entire fastener 60 (breakaway portion 62 and fastening portion 64) is rotating at the high rotational speed, a minimal amount of torque is transmitted through fastener 60, allowing fastener 60 to cut threads into structure 76 even when structure 76 has a torsional resistance that is greater than the torsional strength of fastener 60.

As discussed above, once head 66 of fastener 60 bottoms out on an outer surface of structure 76, an amount of torque required to drive fastener 60 further into structure 76 becomes too great for the kinetic energy force component ($F_k$) of fastener 60 and the torque force component ($F_t$) is increased. Torque may then be transmitted to breakaway region 74 causing breakaway portion 62 to separate from fastening portion 64. Powered driver 12 may then be turned off and breakaway portion 62 may then be ejected from adapter assembly 14 through use of ejector shaft 24.

Several parameters may be varied for driving fastener 60 in the method discussed above. For example, parameters that may be used for the appropriate fastener and driving arrangement according to the method described above may include the major and minor diameters of the threaded shank 72, the body length of threaded shank 72, the pilot hole diameter, the downward force applied to fastener 60, the speed ramp up of powered driver 12, the set speed of powered driver 12, rate of trigger actuation of powered driver 12, and the material properties of structure 76 and fastener 60, such as material densities. More specifically, Table 1 below includes several configurations and associated parameter values for driving fastener 60 in the manner discussed above. The configurations listed below are examples and may generally apply to structure 76 being bone and fastener 60 being formed from a polymer. As indicated above, fastener 60 may be formed from a material that has a greater or lesser torsional strength than the torsional resistance of structure 76. In the examples listed below, the polymer formed fastener 60 may have a torsional strength less than the torsional resistance of bone.

TABLE 1

| major diameter (mm) | body length (mm) | pilot hole diameter (mm) | driver speed (rpm) |
|---|---|---|---|
| 1.5 | 5 | 1.3 | 12,000 |
| 1.5 | 3 | 1.1 | 20,000 |
| 1.5 | 4 | 1.1 | 25,000-30,000 |
| 1.5 | 4 | 1.2 | 25,000-30,000 |
| 1.5 | 5 | 1.1 | 25,000-30,000 |
| 1.5 | 5 | 1.2 | 25,000-30,000 |
| 1.5 | 8 | 1.3 | 25,000-30,000 |

What is claimed is:

1. A method comprising:
   rotating a biocompatible, non-metallic threaded fastener at a rotational speed greater than 15,000 revolutions per minute; and
   driving said fastener into a bone at said rotational speed, said fastener being formed from a material that is softer than said bone.

2. The method of claim 1, wherein rotating said biocompatible, non-metallic threaded fastener includes rotating a fastener formed from one of a polymer, a biocompatible non-resorbable material, a biocompatible resorbable material, a ceramic, a composite material, an allograft and a xenograft.

3. The method of claim 1, further comprising terminating said driving when a predetermined torque limit is applied to said fastener.

4. The method of claim 3, further comprising separating a first portion of said fastener from a second portion of said fastener when said predetermined torque limit is applied to said fastener.

5. The method of claim 1, further comprising separating a first portion of said fastener from a second portion of said fastener when a predetermined torque limit is applied to said fastener.

6. The method of claim 1, further comprising forming a pilot hole having a first diameter greater than a minor diameter of said fastener and less than a major diameter of said fastener, said driving including driving said fastener into said pilot hole.

7. The method of claim 1, wherein a drilling force is applied to said fastener as said fastener is driven into said bone, a total force applied by said fastener being greater than the force required for said cutting and said drilling.

8. The method of claim 1, wherein the first rotational speed is at least 25,000 revolutions per minute.

9. The method of claim 1, wherein said material of said fastener is has a torsional strength that is less than a torsional resistance of said bone.

10. A method comprising driving a biocompatible, non-metallic threaded fastener at a rotational speed greater than 15,000 revolutions per minute into a bone, said rotational speed being based on a material density of said bone relative to a material density of said fastener.

11. The method of claim 10, wherein said fastener is formed from a material that is softer than said bone.

12. The method of claim 10, wherein said material of said fastener is has a torsional strength that is less than a torsional resistance of said bone.

13. The method of claim 12, further comprising terminating said driving when a predetermined torque limit is applied to said fastener.

14. The method of claim 13, further comprising separating a first portion of said fastener from a second portion of said fastener when said predetermined torque limit is applied to said fastener.

15. The method of claim 14, further comprising forming a pilot hole having a first diameter greater than a minor diameter of said fastener and less than a major diameter of said fastener, said driving including driving said fastener into said pilot hole.

16. A method comprising:
    a step for rotating a fastener at a rotational speed greater than 15,000 revolutions per minute; and
    a step for driving said fastener into a bone at said rotational speed, said fastener being formed from a material that is softer than said bone.

17. The method of claim 16, wherein said material of said fastener is has a torsional strength that is less than a torsional resistance of said bone.

18. The method of claim 16, further comprising a step for terminating said driving when a predetermined torque limit is applied to said fastener.

19. The method of claim 18, further comprising a step for separating a first portion of said fastener from a second portion of said fastener when said predetermined torque limit is applied to said fastener.

20. The method of claim 16, further comprising a step for forming a pilot hole having a first diameter greater than a minor diameter of said fastener and less than a major diameter of said fastener, said step for driving including driving said fastener into said pilot hole.

\* \* \* \* \*